United States Patent [19]

Takeda et al.

[11] Patent Number: 4,704,458
[45] Date of Patent: Nov. 3, 1987

[54] PROCESS FOR THE EPIMERIZATION OF AMINATED PHTHALIDEISOQUINOLINES

[75] Inventors: Yoshiyuki Takeda; Osamu Kawashima; Shiro Furukawa; Yasukazu Ogino, all of Kitakyushu, Japan

[73] Assignee: Mitsubishi Chemical Industries Limited, Tokyo, Japan

[21] Appl. No.: 694,160

[22] Filed: Jan. 23, 1985

[30] Foreign Application Priority Data

Feb. 14, 1984 [JP] Japan .................................. 59-25639

[51] Int. Cl.$^4$ ................ C07D 491/056; C07D 217/04; C07D 307/34
[52] U.S. Cl. ..................................... 546/90; 546/139; 549/304; 549/305; 549/307
[58] Field of Search ................................. 546/90, 139

[56] References Cited

FOREIGN PATENT DOCUMENTS 84042305  6/1982  Japan .................................. 546/90
873935   8/1961  United Kingdom ................ 546/139

OTHER PUBLICATIONS

Marjorie et al., Metameconine as a Model Compound in the Study of Aromatic Reactions, pp. 2402-2408, (1962).
"Synthetic Alkaloids Derived from Narcotine", by Echampaty Venkata et al., Proc. Acad, Sci., (United Prov. Agra Ouch), 4, pp. 159-168, (1934).
"Synthetical Experiments in the Group of the isoQuinoline Alkaloids, Part I Anhydrocotarninephthalide", by Edward Hope et al., Journal of the Chemical Society, (1911), vol. XCIX, Part I, pp. 1153 to 1169.
"Synthetical Experiments in the Group of the isoQuinoline Alkaloids, Part IV, The Synthesis of B-Gnoscopine", by Edward Hope et al., Journal of the Chemical Society, (1914), vol. CV, Part II, pp. 2085 to 2105.
"Metallic Derivatives of Alkaloids", by Jitendra Nath Rakshit, Journal of the Chemical Society, (1918), vol. CXIII, pp. 466-471.
"Isocarbostyrils, Part I. Conversion of 8-Alkoxyisocarbostyril-3-Carboxylic Acids into the Related Hydroxy-Esters by Pseudo-Rearrangement", by. J. N. Chatterjea et al., Journal of Indian Chemical Society, vol. 43, No. 10, (1966), pp. 640-647.
"Synthesis of Hydrastine, Part I", by Edward Hope et al., Journal of the Chemical Society, (1931), Part I, pp. 236-247.

Primary Examiner—Henry R. Jiles
Assistant Examiner—J. Richter
Attorney, Agent, or Firm—Cushman, Darby & Cushman

[57] ABSTRACT

Disclosed herein is an improved process for preparing 1RS-3'RS epimer of aminated phthalideisoquinolines represented by the general formula (I):

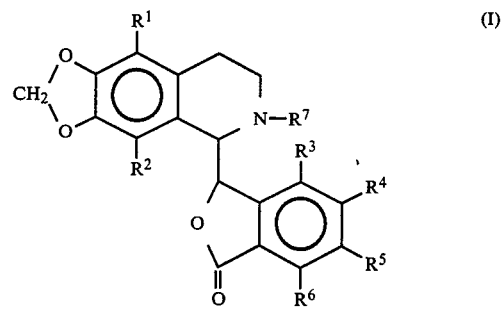

wherein $R^1$ and $R^2$ are independently hydrogen atom or a lower alkoxy group, $R^3$, $R^4$, $R^5$ and $R^6$ are independently hydrogen atom, amino group or a lower alkoxy group with at least one of $R^3$-$R^6$ being amino group, and $R^7$ is a lower alkyl group. The improvement comprises, after having reduced a mixture of epimers of corresponding nitro compounds of the general formula (I) wherein the amino group is replaced by nitro group into the amino compounds (I), treating said amino compound at a temperature in the range of 20°-100° C. in an aliphatic lower alcohol in the presence of an alkali to epimerize 1RS-3'SR epimer of said amino compound into said 1RS-3'RS epimer thereof.

12 Claims, No Drawings

PROCESS FOR THE EPIMERIZATION OF AMINATED PHTHALIDEISOQUINOLINES

FIELD OF THE INVENTION

This invention relates to a process for preparing aminated phthalideisoquinolines.

BACKGROUND OF THE INVENTION

Amino compounds represented by the following general formula (I):

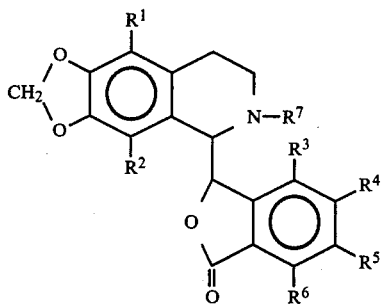

wherein $R^1$ and $R^2$ independently represent hydrogen atom or a lower alkoxy group, $R^3$, $R^4$, $R^5$ and $R^6$ independently represent hydrogen atom, amino group or a lower alkoxy group with at least one of $R^3$–$R^6$ being amino group, and $R^7$ is a lower alkyl group, which are useful for pharmaceutical use, particularly for the treatment of liver or allergic diseases, have two epimers, that is, 1RS-3'RS epimer (hereinafter referred to as A-mer) and 1RS-3'SR epimer (hereinafter referred to as B-mer). They are utilized independently or in a mixture thereof, depending on purpose. It is generally necessary, therefore, to isolate one epimer, for example A-mer, from a reaction mixture for their preparation, when they are to be used singly in the form of A-mer only.

Generally, such amino compounds of the general formula (I) are prepared by reducing nitro compounds represented by the following general formula (II):

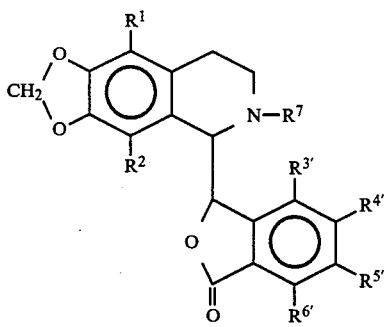

wherein $R^1$, $R^2$ and $R^7$ are as defined above, and $R^{3'}$, $R^{4'}$, $R^{5'}$ and $R^{6'}$ independently represent hydrogen atom, nitro group or a lower alkoxy group with at least one of $R^{3'}$–$R^{6'}$ being nitro group. The nitro compounds of the general formula (II) may be prepared by condensation of tetrahydroisoquinolines represented by the following general formula (III):

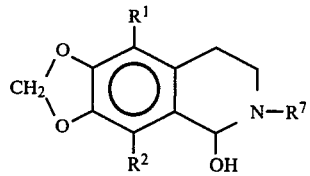

wherein $R^1$, $R^2$ and $R^7$ are as defined above, with nitrophthalides represented by the following general formula (IV):

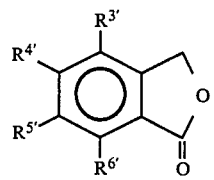

wherein $R^{3'}$–$R^{6'}$ are as defined above.

In the condensation reaction of the tetrahydroisoquinolines and the nitrophthalides, the nitro compounds of the general formula (II) are obtained in the form of a mixture of A-mer and B-mer. When the mixture is then reduced, the resulting amino compounds of the general formula (I) are obtained, of course, in the form of a mixture of A-mer and B-mer. Therefore, it is desirable to increase the yield of A-mer by preventing the formation of B-mer in the condensation procedure, when only A-mer is required.

In order to efficiently obtain A-mer of the amino compounds of the general formula (I), there has been proposed a method which comprises epimerization of B-mer into A-mer of the nitro compounds of the general formula (II) by a certain treatment of the mixture obtained by the condensation of the tetrahydroisoquinolines of the general formula (III) and the nitrophthalides of the general formula (IV).

In such a method, however, the nitro compounds may be partly decomposed in the epimerization process, although the epimerization of B-mer into A-mer may be certainly performed well. In addition to such a defect, there is a problem of safety due to the nitro group in the molecule when B-mer is to be recycled to the epimerization process after separation of A-mer from the epimerized mixture.

It has generally been considered that such an epimerization may proceed in a compound having an electron attracting group such as nitro group in the phthalide ring and, on the other hand, a compound having an electron donating group such as amino group is not well processed in such an epimerizaton process. This is the reason why the epimerization has been carried out on the nitro compounds of the general formula (II), not on the amino compounds of the general formula (I), in such a method as above-described even though there are some demerits mentioned above.

In consideration of such circumstances, the present inventors have made great efforts on the study of a process for efficient preparation of A-mer of the amino compounds represented by the formula (I) and finally found that, when treated under special conditions, such amino compounds which have been considered to be difficulty epimerized can be in fact processed, so that the B-mer can well be converted into the A-mer without any significant decomposition of the amino compounds.

SUMMARY OF THE INVENTION

The present invention provides an improved process for preparation of aminated phthalideisoquinolines. The process of the invention comprises preparing an epimer, A-mer, of the amino compounds represented by the following general formula (I):

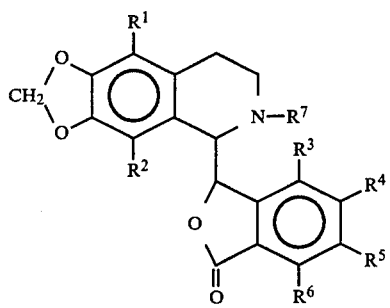
(I)

wherein $R^1$ and $R^2$ independently represent hydrogen atom or a lower alkoxy group, $R^3$, $R^4$, $R^5$ and $R^6$ independently represent hydrogen atom, amino group or a lower alkoxy group with at least one of $R^3$–$R^6$ being amino group, and $R^7$ is a lower alkyl group, from a mixture of two epimers, A-mer and B-mer, of the nitro compounds represented by the following general formula (II):

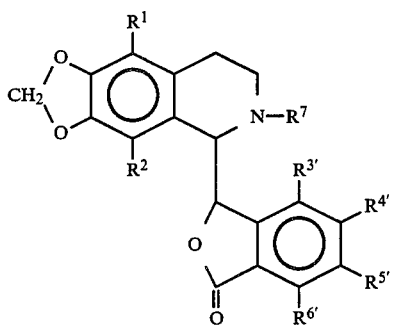
(II)

wherein $R^1$, $R^2$ and $R^7$ are as defined above, and $R^{3'}$, $R^{4'}$, $R^{5'}$ and $R^{6'}$ independently represent hydrogen atom, nitro group or a lower alkoxy group with at least one of $R^{3'}$–$R^{6'}$ being nitro group. The improvement of the process of the invention comprises, after having reduced the nitro compound of the general formula (II) into the amino compound of the general formula (I), this amino compound is then treated at a temperature of 20°–100° C. in an aliphatic lower alcohol in the presence of an alkali to epimerize B-mer into A-mer of the amino compound.

DESCRIPTION OF THE INVENTION

The invention will hereinafter be described in more detail.

The terms "lower alkyl group" and "lower alkoxy group" herein refer to in general those having 1–5 carbon atoms.

Preferred amino compounds of the general formula (I) which may be prepared in the invention may be those in which, for example, $R^1$ and $R^2$ are hydrogen atom or methoxy or ethoxy group, either $R^3$ or $R^6$ is amino group and the rest of $R^3$–$R^6$ are hydrogen atom or methoxy or ethoxy group, and $R^7$ is methyl group. The most preferred amino compound in the invention is tritoqualine represented by the following formula (V):

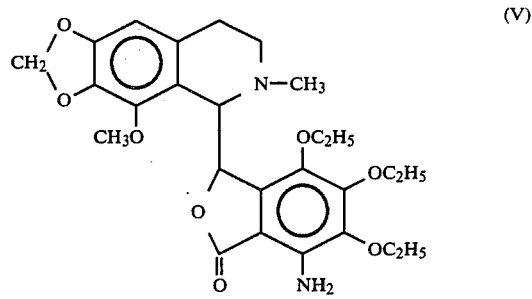
(V)

Condensation Step

The amino compounds of the general formula (I) are prepared by reduction of the nitro compounds of the general formula (II) in the present invention. The nitro compounds (II) may usually be prepared by condensation of tetrahydroisoquinolines represented by the following general formula (III):

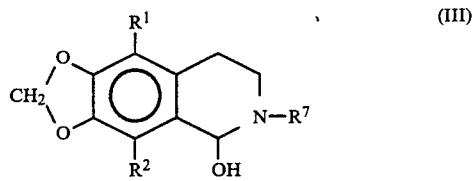
(III)

wherein $R^1$, $R^2$ and $R^7$ are as defined above, with nitrophthalides represented by the following general formula (IV):

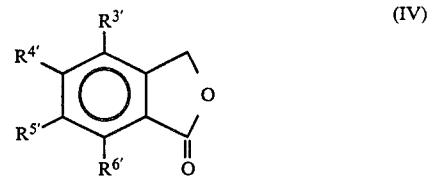
(IV)

wherein $R^{3'}$–$R^{6'}$ are as defined above.

The condensation is generally carried out at a temperature in the range of 20°–100° C., preferably 40°–80° C., for approximately 1–3 hours in an alcohol such as methanol, ethanol, propanol, butanol and the like.

The reaction rate may unsuitably be slow with too low temperatures, while undesirable decomposition of the starting material, tetrahydroisoquinoline, may occur if the temperature is too high.

In the reaction, either A-mer or B-mer of the nitro compound can be produced, depending on the difference in the configuration, RS or SR, of hydrogen atom at the condensing position, that is, of hydrogen atom bonded to the carbon atom at 1-position of the tetrahydroisoquinoline or 3′-position of the nitrophthalide. Thus, there may generally be obtained a mixture of A-mer and B-mer of the nitro compounds. Longer the reaction period, higher the ratio of A-mer but lower the yield of the nitro compound. In the present invention, however, the ratio of A-mer in the nitro compound produced in this condesnation step is not especially limited, since the produced B-mer can be well converted into A-mer in the later step described hereinbelow. The ratio of A-mer in the nitro compound may usually be in the range of approximately 20-80% by mole.

The amount of the tretrahydroisoquinoline used may generally be in the range of 0.8-1.2 times by mole, preferably 0.9-1.0 times by mole, based on the amount of the nitrophthalide used. Smaller amount results in a low yield of the nitro compound while an amount more than the upper limit may cause undesirable decomposition of the tetrahydroisoquinoline.

Generally, the crystal nitro compounds can easily be collected by crystallization by cooling or water-dilution of the reaction mixture at the end of this step.

Reduction Step

According to the present invention, the nitro compounds of the general formula (II) in the form of a mixture of A-mer and B-mer obtained in the condensation step above may be subjected to reduction to convert them into the corresponding amino compounds of the general formula (I): prior to the epimerization step described below:

The nitro compound may be reduced by any of the following procedures: (i) reduction using a metal borohydride as a reducing agent in the presence of a catalyst selected from metals of the IB and VIII groups and compounds thereof; (ii) reduction using as a reducing agent a combination of metal or a salt thereof having a low valence and an acid; (iii) catalytic hydrogenation using a platinum group metal or a compound thereof; (iv) reduction using $LiAlH_4$, $NaBH_2S_3$ or $NaBH_3(OH)$ as a reducing agent in the absence of any catalyst.

Particularly preferred industrial method may be the procedure (i) wherein this reaction can proceed well at normal pressure and the desired product can easily be separated from the reaction mixture after the reduction step.

Some examples of the catalysts which may be used in the reduction procedure (i) include, for example, metals such as Cu, Ag, Ni, Pd, Pt, Co, Rh, Ru and the like, preferably Cu, inorganic acid salts thereof such as hydrochlorides and sulfates, organic acid salts thereof such as acetates, complexes thereof with phosphine, pyridine, acetylacetone or the like, hydroxides thereof, oxides thereof, or the like. When copper or a compound thereof is used as the catalyst, nickel or a compound thereof may be more preferably utilized theretogether in an atomic ratio, Ni/Cu, of 400-8,000 ppm. The catalyst may generally be used in an amount in the range of 0.1-40% by mole, preferably 1-10% by mole, based on the nitro compound.

Some illustrative examples of the reducing agent which may be used in the procedure (i) include, for example, $NaBH_4$, $LiBH_4$, $NaBH_3CN$, $NaBH_2S_3$, $NaBH(OCH_3)_3$, $NaBH_3(OH)$, $KBH_4$, $Ca(BH_4)_2$ or the like. The reducing agent may usually be used in an amount of 1.1-3 times by mole, preferably 1.5-2 times by mole, based on the nitro compound. Generally, the reducing agent may be utilized in the form of a solution in an aqueous or alcoholic caustic alkali.

In the mixture obtained in the procedure (i), a major portion of the desired amino compound and most of the metal components used as a catalyst are generally precipitated in the solvent. Also, the mixture contains a small amount of the remaining reducing agent.

Preferably, a mineral acid such as hydrochloric acid, sulfuric acid and the like is added and molecular oxygen, such as air, is blown into the reaction mixture after the reduction procedure (i) in the present invention. This results in the decomposition of the remaining reducing agent into boric acid and hydrogen and in the dissolution of the precipitated metal components. The acid may generally be added in such an amount that the pH of the mixture becomes 3 or less. The air-blowing is continued until the metal components are substantially totally dissolved. Usually, the amount of air is 0.1-5 times by volume based on the mixture. This treatment is generally carried out at a temperature of 10°-60° C.

The mixture should then be neutralized with ammonia before it is extracted with an organic solvent to recover the produced amino compound in an organic phase; otherwise, the amino compounds in the mixture cannot be extracted in the organic phase since they are in the form of a mineral acid salt. By the addition of ammonia, the mineral acid salt of the amino compound may be converted into the free form while the metal components are converted into a water-soluble amine complex. Generally, ammonia is used in the form of aqueous ammonia with a concentration of 5-30% by weight and in such an amount that the pH of the mixture may be 8 or more.

The thus treated mixture is subjected to extraction with an organic solvent. The solvent used may be a water-immiscible solvent in which the amino compounds can be dissolved well, and includes, preferably, halogenated hydrocarbons such as dichloromethane, chloroform, dichloroethane, chlorobenzene and the like. The amount of the solvent may usually be in the range of 0.5-4 times by weight based on the reaction mixture.

The organic solvent for extraction may be preliminarily added to the mixture after the reduction. In this case, the acid-treatment, air-blowing and ammonia-treatment described above are carried out in the presence of the organic solvent for extraction.

Occasionally, the reduced mixture, may be mixed directly with a halogenated hydrocarbon to dissolve the product, amino compound, followed by filtering the mixture to separate the catalyst.

The amino compounds may then be isolated from the thus collected organic phase. Generally, a solvent in which the amino compounds are less soluble, for example, alcohols, aliphatic or aromatic hydrocarbons, water or the like, is added to the organic phase. The substitution of the solvent may result in deposition of the amino compound crystal which can be collected in turn by filtration. Preferably, a solvent having a boiling point higher than the solvent in which the amino compound has been dissolved may be used as the solvent to be added since the solvent-substitution can be readily performed through distillation. Further, if aliphatic lower alcohols such as methanol, ethanol, propanol and the like are utilized as the solvent to be added, the treated mixture can directly be subjected to the subsequent epimerization step described below immediately after the treatment or after distilling off the halogenated hydrocarbon.

When the nitro compound is reduced in the procedure (ii), a combination of a metal such as Sn, Fe, Zn and the like or a compound thereof with hydrochloric acid may generally be used as a reducing agent. The metal or compound thereof and the acid may usually be used in combination, each in an amount of 3-20 times by mole, respectively, based on the nitro compound.

In the reduction procedure (ii), a large amount of the metal components used as a reducing agent and the product amino compound are precipitated in the reduced mixture. Generally, after neutralizing the mixture with addition of caustic alkali, the mixture is extracted with a water-immiscible organic solvent in which the amino compound can be well dissolved. The thus extracted organic phase containing the amino compound may then be treated in the same manner as described above for the procedure (i). In this procedure (ii), it is necessary to perform the extraction of the mixture containing a large amount of the precipitated metal components and, after extraction, to filter off the fine metal component particles from the water phase. Thus, this procedure (ii) is somewhat troublesome one for an industrial process.

Generally speaking, these reduction procedures are carried out at a temperature in the range of 0°-100° C., preferably 20°-60° C., although the temperature can slightly vary with the procedures. Higher temperatures may yield a larger amount of by-products. On the contrary, a lower temperature will give slower reaction rate and, therefore, the desired product, amino compounds, cannot efficiently be obtained. The reaction period is usually 10 minutes to 4 hours.

The reduction may generally be carried out in a solvent which may slightly vary depending on each procedure, for example, an aliphatic alcohol such as methanol, ethanol and propanol, an ether such as diglyme and tetrahydrofuran, an aliphatic ketone such as acetone and methyl ethyl ketone, a water-miscible organic solvent such as dimethylformamide and dimethylsulfoxide, an aqueous solution thereof, or the like. When a metal borohydride is used as a reducing agent, an aliphatic lower alcohol may be particularly preferred since the mixture can immediately be subjected to the subsequent epimerization step described below. The solvent may generally be utilized in an amount of 2-50 times by weight, preferably 3-20 times by weight, based on the nitro compound (II). The nitro compounds may also be supplied in the form of a solution in acetone or acetic acid, for example.

Epimerization Step

In the present invention, the amino compounds (I) should be epimerized in an aliphatic lower alcohol in the presence of an alkali after the reduction step.

The reduced mixture to be epimerized may contain both A-mer and B-mer in a molar ratio of 10:90 to 80:20.

The aliphatic alcohols which may be used in the invention include those having 1-5 carbon atoms such as methanol, ethanol, propanol, butanol nd the like, with methanol and ethanol being preferred. They may also contain some water. The solvents may usually be used in an amount of 3-20 times by weight based on the amount of the amino compounds.

This step may be generally carried out at a temperature in the range of 20°-100° C., preferably 50°-80° C. Lower or higher temperatures cannot result in a desired A-mer content.

The alkali which may be used in this step generally includes alkali hydroxides such as sodium hydroxide, potassium hydroxide and barium hydroxide, alkali alkoxides such as sodium alcoholate, or the like. These may be used in a concentration of 1-5% by weight, preferably 2-5% by weight. Lower concentration will cause a slow reaction rate and higher concentration may give a low yield. The alkali may generally be utilized in an amount of 0.4-3 times by mole, preferably 0.9-2 times by mole, based on the B-mer to be epimerized.

The epimerization period may be varied depending on the temperature and the alkali used, and is usually 2-20 hours.

The epimerization step may be generally carried out by adding the amino compound into a solvent containing a predetermined amount of an alkali and treating the mixture under the predetermined conditions with stirring. In these conditions, although B-mer may be dissolved, A-mer can hardly be dissolved and remains as crystals. In the invention, therefore, the mixture can be treated either directly in the form of a slurry or after preliminarily separating the precipitated A-mer. Further, since the epimerized mixture contains both the precipitated A-mer and the dissolved B-mer, the desired A-mer can be obtained by solid-liquid separation of the mixture.

In the invention, the A-mer of the amino compound (I) can preferably be recovered in a high purity, for example up to 95% or more, by a simple filtration in the final step. Of course, the collected crystals, A-mer of the amino compound, may be washed with, for example, an aliphatic alcohol or water, if necessary.

Thus, B-mer of the amino compounds can be well converted into the desired A-mer by such an epimerization step in accordance with the present invention. These findings are surprising in view of the fact that it has been considered that epimerization of such a compound having an electron donor group such as amino group on the phthalide ring is difficult to perform. Further, the amino compounds may hardly be decomposed in the epimerization step. Also, the B-mer in the resultant mixture can safely be recycled to the epimerization step after removing A-mer. Thus, the process of this invention is a very advantageous industrial process.

DESCRIPTION OF THE PREFERRED EMBODIMENTS

The invention will hereinafter be illustrated more fully and clearly with the following examples. These are not construed as limiting examples, and many modifications and variations will be included in the invention without departing from the scope thereof defined in the appended claims.

EXAMPLES 1-2

Condensation

In to a 300 ml glass reaction vessel having a stirrer and a temperature controller, 23.7 g (100 m mol) of tetrahydroisoquinoline, called cotarnine, which is represented by the general formula (III) wherein $R^1$ is hydrogen atom, $R^2$ is methoxy group and $R^7$ is methyl group, 25.3 g (100 m mol) of nitrophthalide, which is represented by the general formula (IV) wherein $R^{3'}$ is nitro group, $R^{4'}$ is hydrogen atom, $R^{5'}$ is methoxy group and $R^{6'}$ is ethoxy group, and 150 ml of methanol were charged, and the reaction was carried out at 63° C. for 2 hours under stirring.

After completion of the reaction, 50 ml of water was added to the mixture and this was cooled to 20° C. to recover the desired product corresponding to the following formula:

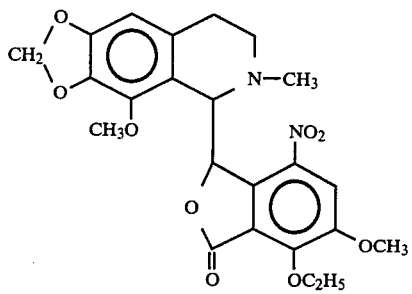

The yield of the desired product was 56.5% based on the starting cotarnine and the A-mer content was 42% and the B-mer content 58% in the product.

Reduction

Into a 500 ml glass reaction vessel similar to the above-described vessel, 26.5 g (56.1 m mol) of the condensation product obtained above, 20 g of tin powder, 160 ml of acetone and 100 ml of water were charged, and 90 ml of 35% hydrochloric acid was dropwise added to the mixture under stirring over a period of 30 minutes while maintaining at 5° C. The mixture was then heated to 25° C. where the reaction was continued for additional one hour.

After completion of the reaction, the mixture was neutralized with an aqueous solution of sodium hydroxide. The slurry containing the solid product was extracted with dichloroethane and the solvent was distilled off to recover the reduced product with a yield of 58.2%.

Epimerization:

Into the similar 500 ml glass reaction vessel, 13.2 g of the amino compounds obtained above which contained 42% of A-mer and 58% of B-mer, 100 ml of ethanol and an alkali shown in Table 1 below were charged. After stirring under the conditions shown in Table 1, the mixture was filtered to collect the crystal of A-mer.

The contents of A-mer and B-mer in the resulting mixture, the decomposition rate of the amino compound and the purity in A-mer of the recovered crystal were determined. The results are shown in Table 1.

TABLE 1

| Ex. No. | Alkali Kind | Alkali Conc. (wt %) | Conditions Temp. (°C.) | Conditions Period (hr) | Content A-mer (%) | Content B-mer (%) | Decomp. Rate (%) | A-mer Purity (%) |
|---|---|---|---|---|---|---|---|---|
| 1 | KOH | 2.5 | 60 | 7 | 92 | 8 | 7.3 | 98 |
| 2 | NaOH | 2.5 | 60 | 7 | 92 | 8 | 6.5 | 96 |

EXAMPLES 3–4

The procedures of Example 1 were repeated except that the condensation reaction was carried out for 1.5 hours. The obtained condensation product contained 12% of A-mer and 88% of B-mer. The results are shown in Table 2.

TABLE 2

| Ex. No. | Alkali Kind | Alkali Conc. (wt %) | Conditions Temp. (°C.) | Conditions Period (hr) | Content A-mer (%) | Content B-mer (%) | Decomp. Rate (%) | A-mer Purity (%) |
|---|---|---|---|---|---|---|---|---|
| 3 | KOH | 3.5 | 60 | 9 | 92.5 | 7.5 | 8.9 | 98 |
| 4 | NaOH | 3.2 | 70 | 6 | 90 | 10 | 9.3 | 97 |

EXAMPLES 5–8

The procedures of Example 1 were repeated except that the nitrophthalide of Example 1 was replaced by nitrophthalide represented by the general formula (IV) wherein $R^{3'}$, $R^{4'}$ and $R^{5'}$ are ethoxy groups and $R^{6'}$ is nitro group. In these examples the condensation products had the following formuls (VI):

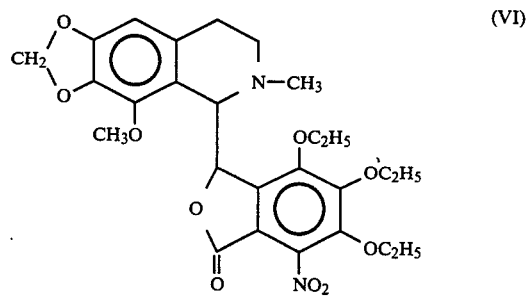

(VI)

In Examples 5 and 6, A-mer content was 40.5% and B-mer content 59.5%, while A-mer conteTnt was 14% and B-mer content 86% in Examples 7 and 8. he results are shown in Table 3.

TABLE 3

| Ex. No. | Alkali Kind | Alkali Conc. (wt %) | Conditions Temp. (°C.) | Conditions Period (hr) | Content A-mer (%) | Content B-mer (%) | Decomp. Rate (%) | A-mer Purity (%) |
|---|---|---|---|---|---|---|---|---|
| 5 | KOH | 2.5 | 60 | 7 | 90.5 | 9.5 | 8.8 | 96.5 |
| 6 | NaOH | 2.5 | 60 | 7 | 90.5 | 9.5 | 7.5 | 95.5 |
| 7 | KOH | 3.5 | 70 | 6 | 88 | 12 | 10 | 96 |
| 8 | NaOH | 1.5 | 60 | 11 | 91 | 9 | 4.8 | 88 |

EXAMPLE 9

Condensation:

Into a 200 ml glass reaction vessel having a stirrer and a temperature controller, 23.7 g (100 m mol) of tetrahydroisoquinoline, called cotarnine, which is represented by the general formula (III) wherein $R^1$ is hydrogen atom, $R^2$ is methoxy group and $R^7$ is methyl group, 31.1 g (10 m mol) of nitrophthalide represented by the general formula (IV) wherein $R^{3'}$, $R^{4'}$ and $R^{5'}$ are ethoxy groups and $R^{6'}$ is nitro group and 80 ml of methanol were charged and the reaction was carried out at 60° C. for 2 hours under stirring.

After completion of the reaction, the mixture was cooled to 20° C. to recover the precipitated product having the following structural formula (VI):

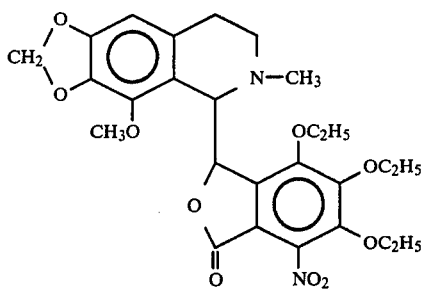

The yield of the desired product was 75% based on the starting contarnine and the A-mer content was 46% and B-mer content 54%.

Reduction:

Into a similar 200 ml glass reaction vessel, 26.5 g (50 m mol) of the nitro compound obtained above, 0.88 g (3.5 m mol) of copper sulfate, 2.3 mg (0.009 m mol) of nickel sulfate, with Ni/Cu=2,560 ppm, and 80 ml of methanol were charged, and 3.8 g (100 m mol) of sodium borohydride dissolved in 35 ml of methanolic 1N sodium hydroxide solution was dropwise added to the mixture under stirring over a period of one hour while maintaining at 35° C. The reaction was further continued at the same temperature under stirring for one hour. Analysis of the product in the resultant mixture showed the conversion rate of 99% and selectivity of 99%.

Separation of Amino Compounds

After adding 50 ml of 35% hydrochloric acid to the mixture obtained above to the pH of 2 in order to decompose the remaining excess sodium borohydride, copper was oxidised by blowing air thereinto. Then, 60 ml of 28% aqueous ammonia and 50 ml of water was added to adjust the pH of the mixture to 9.2. This converted the amino compound into the free form while copper formed amine complex with ammonia. The mixture was then extracted with 160 ml of dichloromethane. Thus, the amino compound was well extracted into the organic phase, while the metal components remained in water layer, not giving any deposit. In these procedures, methanol was totally distributed into the water layer while the product was recovered into the organic phase with a yield of approximately 100%.

To the obtained solution of the amino compound in dichloromethane, 480 ml of methanol was added and the solvent was distilled off to concentrate to the solvent volume of 100 ml. Thus, methanol was substituted for dichloromethan.

Epimerization

Into a similar 200 ml glass reaction vessel, the obtained methanol slurry containing 24.6 g of the amino compound, and 4.4 g of sodium hydroxide were charged. After the reaction was carried out at 60° C. under stirring for 10 hours, the mixture was filtered to recover the crystal of A-mer.

The resulting reaction mixture contained 23.0 g (content of 96.6%) of A-mer and 0.8 g (content of 3.4%) of B-mer. The collected crystal (A-mer) had a purity of approximately 100%. The yield of the A-mer was 91% based on the nitro compound used as a starting material.

These reaction conditions and the results are listed in Table 4 below.

EXAMPLES 10-12

The procedures of Example 9 were repeated except that the epimerization was carried out under the conditions shown in Table 4. The results are shown in Table 4.

TABLE 4

| Ex. No. | Alkali Kind | Alkali Conc. (wt %) | Conditions Temp. (°C.) | Conditions Period (hr) | Content A-mer (%) | Content B-mer (%) | Decomp. Rate (%) | A-mer Purity (%) |
|---|---|---|---|---|---|---|---|---|
| 9 | NaOH | 5.5 | 60 | 10 | 96.6 | 3.4 | 2.0 | 100 |
| 10 | KOH | 5.0 | 60 | 8 | 96.0 | 4.0 | 2.4 | 100 |
| 11 | NaOH | 2.7 | 70* | 5 | 93.0 | 7.0 | 2.7 | 100 |
| 12 | KOH | 2.7 | 75* | 4 | 88.0 | 12.0 | 3.5 | 98 |

*in ethanol

COMPARATIVE EXAMPLES 1-3

The procedures of Example 9 were repeated except that methanol used for epimerization in Example 9 was replaced by water of the same volume and the epimerization was carried out under the conditions shown in Table 5. The results are shown in Table 5.

TABLE 5

| Ex. No. | Alkali Kind | Alkali Conc. (wt %) | Conditions Temp. (°C.) | Conditions Period (hr) | Content A-mer (%) | Content B-mer (%) | Decomp. Rate (%) | A-mer Purity (%) |
|---|---|---|---|---|---|---|---|---|
| 1 | NaOH | 5.5 | 60 | 10 | 49 | 51 | 27.5 | 49 |
| 2 | NaOH | 5.5 | 80 | 10 | 52 | 48 | 42 | 52 |
| 3 | KOH | 7 | 80 | 10 | 51 | 49 | 44 | 51 |

What is claimed is:

1. In a process for the preparation of tritoqualine, comprising preparing a 1RS-3'RS epimer of an amino compound represented by the structural formula (V):

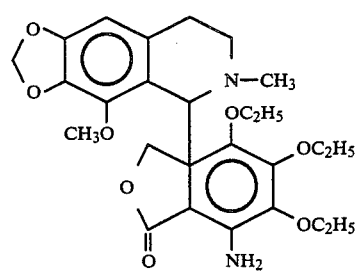

(V)

from a mixture of a 1RS-3'RS epimer and a 1RS-3'SR epimer of a nitro compound represented by the structural formula (VI):

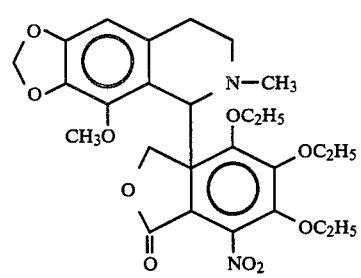

(VI)

reducing the nitro compound of the structural formula (VI) to the amino compound of the structural formula (V), wherein the improvement comprises treating said amino compound at a temperature in the range of 20° C. to 100° C. in an aliphatic lower alcohol in the presence of an alkali to epimerize a 1RS-3′SR epimer of the amino compound to said 1RS-3′RS epimer thereof.

2. The process as defined in claim 1, wherein the aliphatic lower alcohol for the epimerization is methanol or ethanol.

3. The process as defined in claim 1, wherein the alkali for the epimerization is an caustic alkali.

4. The process as defined in claim 1, wherein the epimerization is carried out for a period of 2-20 hours.

5. The process as defined in claim 1, wherein the aliphatic lower alcohol for the epimerization is used in an amount of 3-20 times by weight larger than the amount of the amino compound of the general formula (V).

6. The process as defined in claim 1, wherein the alkali for the epimerization is used in a concentration of 1-5% by weight.

7. The process as defined in claim 1, wherein the alkali for the epimerization is used in an amount of 0.4-3 times by mole based on the 1RS-3′SR epimer of the amino compound to be epimerized.

8. the process as defined in claim 1, wherein the epimerization is carried out at a temperature in the range of 50°-80° C.

9. The process as defined in claim 1, wherein the amino compound to be epimerized contains the 1RS-3′RS epimer and the 1RS-3′SR epimer in a molar ratio of 10 : 90 to 80 : 20.

10. The process as defined in claim 1, wherein the epimerized mixture is filtered to collect a crystal containing 95% by mole or more of the 1RS-3′RS epimer of the amino compound.

11. The process as defined in claim 1, wherein the nitro compound of the general formula (VI) is reduced with a metal borohydride as a reducing agent and a metal of the IB or VIII group or a compound thereof as a catalyst.

12. The process as defined in claim 1, wherein an aliphatic lower alcohol is added to the collected organic phase, the halogenated hydrocarbon is distilled off, and the obtained slurry is then epimerized.

* * * * *